USOO5760002A

United States Patent [19]
McIver

[11] Patent Number: 5,760,002
[45] Date of Patent: Jun. 2, 1998

[54] DIFLOURO PENTAPEPTIDE DERIVATIVE ANTI-INFLAMMATORY AGENTS

[75] Inventor: John McMillan McIver, Cincinnati, Ohio

[73] Assignee: The Proctor & Gamble Company, Cincinnati, Ohio

[21] Appl. No.: 318,179

[22] Filed: Oct. 5, 1994

Related U.S. Application Data

[63] Continuation of Ser. No. 995,217, Dec. 22, 1992, abandoned.

[51] Int. Cl.$^6$ .............................. A61K 38/00; C07K 7/06; C07K 7/00
[52] U.S. Cl. ........................ 514/17; 530/329; 530/330
[58] Field of Search ........................ 530/330; 514/17

[56] References Cited

U.S. PATENT DOCUMENTS

| | | | |
|---|---|---|---|
| 4,242,329 | 12/1980 | Claeson et al. | 424/177 |
| 4,316,889 | 2/1982 | Bajusz et al. | 424/177 |
| 4,399,065 | 8/1983 | Bajusz et al. | 260/112.5 |
| 4,401,594 | 8/1983 | Umezawa et al. | 260/112.5 |
| 4,478,745 | 10/1984 | Bajusz et al. | 260/112.5 |
| 4,528,133 | 7/1985 | Kasafirek et al. | 260/112.5 |
| 4,596,789 | 6/1986 | Dutta et al. | 514/18 |
| 4,623,639 | 11/1986 | Hassall et al. | 514/18 |
| 4,703,036 | 10/1987 | Bajusz et al. | 514/18 |

(List continued on next page.)

FOREIGN PATENT DOCUMENTS

| | | |
|---|---|---|
| A-52881/86 | 2/1985 | Australia. |
| 0275101 | 7/1988 | European Pat. Off.. |
| 0 293 881 | 12/1988 | European Pat. Off.. |
| 0 313 969 | 5/1989 | European Pat. Off.. |
| 0 397 427 | 11/1990 | European Pat. Off.. |
| 47-30618 A/T | 11/1972 | Japan. |
| 57-145846 A | 7/1974 | Japan. |
| 58-164563 A | 3/1982 | Japan. |
| 866642 | 9/1986 | South Africa. |
| 2 171 103 | 8/1986 | United Kingdom. |
| 84/00365 | 2/1984 | WIPO. |
| WO 86/06379 | 11/1986 | WIPO. |
| 87/02675 | 5/1987 | WIPO. |

OTHER PUBLICATIONS

Aoyagi, et al. "Biological Activities of Leupeptins", *The Journal of Antibiotics*, vol. 22, pp. 558–568 (1969).
Bajusz, et al. "Inhibition of Thrombin and Trypsin by Tripeptide Aldehydes", *Int. J. Peptide Protein Res.*, vol. 12, pp. 217–221 (1978).
Gaal, et al. "Cationic Ferritin Uptake by Cultured Anterior Pituitary Cells Treated with the Proteinase Inhibitor, BOC–DPhe–Phe–Lys–H", *Histochemistry*, vol. 88, pp. 401–406 (1988).
Makara, et al. "The Tripeptide Aldehyde, Boc–DPhe–Phe–Lysinal, is a Novel Ca$^{2+}$ Channel Inhibitor in Pituitary Cells", *European Journal of Pharmacology*, vol. 151, pp. 147–149 (1988).

Nagy, et al. "Tripeptide Aldehyde Protease Inhibitors May Depress in Vitro Prolactin and Growth Hormone Release", *Endocrinology*, vol. 116, pp. 1426–1432 (1985).
Rappay, et al. "Various Proteinase Inhibitors Decrease Prolactin and Growth Hormone Release by Anterior Pituitary Cells", *Life Sciences*, vol. 36, pp. 549–555 (1985).

*Primary Examiner*—Cecilia J. Tsang
*Assistant Examiner*—S. G. Marshall
*Attorney, Agent, or Firm*—Bart S. Hersko; David L. Suter; Jacobus C. Rasser

[57] ABSTRACT

The subject invention involves anti-inflammatory compounds having the following structure:

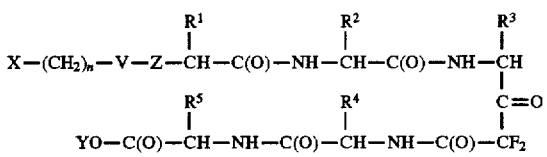

wherein:

a) —X is cyclic alkyl, having from 4 to 15 carbon atoms; branched alkyl, having from 6 to 15 carbon atoms; or aryl having from 6 to 15 carbon atoms;

b) n is an integer from 0 to 2;

c) —V— is —OC(O)—, —N(Q)C(O)—, —N(Q)C(S)—, —C(O)—, —SO2— or —P(O)(OH)—;

d) —Q is hydrogen; or straight or branched chain alkyl, saturated or unsaturated with 1 or 2 double bonds, having from 1 to 6 carbon atoms; or —Q and —X are covalently linked forming a cyclic moiety which includes the nitrogen to which —Q is bonded and from 5 to 20 carbon atoms;

e) Z is —O— or —NH—; when V is —OC(O)—, —Z— is —NH—;

f) —R1 is a hydrophobic moiety;

g) —R2 is a hydrophobic moiety;

h) —R3 is —(CH2)m—A—NH2 or —(CH2)m—A—B—C(NH2)=NH wherein m is an integer from 1 to about 6, —A— is a covalent bond or p-phenyl or p-cyclohexyl, and —B— is a covalent bond or —NH—;

i) —R4 is a hydrophobic moiety;

j) —R5 is —(CH2)m—A—NH2 or —(CH2)m—A—B—C(NH2)=NH wherein m is an integer from 1 to about 6, —A— is a covalent bond or p-phenyl or p-cyclohexyl, and —B— is a covalent bond or —NH—; and k) —Y is hydrogen or methyl.

The subject invention also involves pharmaceutical compositions comprising the above compounds, and methods for treating inflammation or pain using such compounds and compositions.

17 Claims, No Drawings

U.S. PATENT DOCUMENTS

| | | | |
|---|---|---|---|
| 4,816,449 | 3/1989 | Hahn | 514/17 |
| 4,845,242 | 7/1989 | Powers et al. | 549/283 |
| 4,873,221 | 10/1989 | Trainor | 514/18 |
| 4,880,780 | 11/1989 | Trainor et al. | 514/18 |
| 4,883,863 | 11/1989 | Abe et al. | 530/331 |
| 4,902,781 | 2/1990 | Mizoue et al. | 530/331 |
| 4,923,890 | 5/1990 | Trainor et al. | 424/46 |
| 5,036,054 | 7/1991 | Kaltenbronn et al. | 514/19 |
| 5,066,642 | 11/1991 | Vranesic et al. | 514/18 |
| 5,066,643 | 11/1991 | Abeles et al. | 514/18 |

1

DIFLOURO PENTAPEPTIDE DERIVATIVE ANTI-INFLAMMATORY AGENTS

This is a continuation of application Ser. No. 07/995,217, filed on Dec. 22, 1992, now abandoned.

TECHNICAL FIELD

The subject invention relates to novel peptide derivatives which are useful as anti-inflammatory agents.

BACKGROUND OF THE INVENTION

Certain polypeptide derivatives having various biological activities are known. The following references disclose such polypeptide derivatives: U.S. Pat. No. 4,242,329 issued to Claeson, Simonsson & Arielly on Dec. 30, 1980; U.S. Pat. No. 4,316,889 issued to Bajusz, Hasenohrl, Barabas & Bagdy on Feb. 23, 1982; U.S. Pat. No. 4,399,065 issued to Bajusz, Hasenohrl, Barabas & Bagdy on Aug. 16, 1983; U.S. Pat. No. 4,401,594 issued to Umezawa, Takeuchi, Aoyagi, Ishii, Saino & Someno on Aug. 30, 1983; U.S. Pat. No. 4,478,745 issued to Bajusz, Hasenohrl, Barabas & Bagdy on Oct. 23, 1984; U.S. Pat. No. 4,528,133 issued to Kasafirek, Fric, Slaby & Robalova on Jul. 9, 1985; U.S. Pat. No. 4,596,789 issued to Dutta, Stein, Trainor & Wildonger on Jun. 24, 1986; U.S. Pat. No. 4,623,639 issued to Hassall, Johnson & Roberts on Nov. 18, 1986; U.S. Pat. No. 4,703,036 issued to Bajusz, Hasenohrl, Bagdy, Barabas, Dioszegi, Fittler, Jozsa, Horvath & Jozst on Oct. 27, 1987; U.S. Pat. No. 4,880,780 issued to Trainor & Stein on Nov. 14, 1989; U.S. Pat. No. 4,883,863 issued to Abe, Yaginuma, Nagasawa & Kuroiwa on Nov. 28, 1989; U.S. Pat. No. 4,902,781 issued to Mizoue, Okazaki, Hanada, Omura & Amamoto on Feb. 20, 1990; U.S. Pat. No. 4,923,890 issued to Trainor & Stein on May 8, 1990; U.S. Pat. No. 5,066,643 issued to Abeles & Gelb on Nov. 19, 1991; PCT Patent Application No. 84/00365 of Galpin & Wilby, published Feb. 2, 1984; PCT Patent Application No. 87/02675 of Hoover, published May 7, 1987; Japanese Patent Application No. 47-30618 of Toray Inds. Inc., published Nov. 9, 1972; Japanese Patent Application No. 57-145846 of Mitsubishi Chem. Ind. KK, published Jul. 19, 1974; Japanese Patent Application No. 58-164563 of Daiichi Kagaku Yaku, published Mar. 25, 1982; European Patent Application No. 0275101 of Merrell Dow Pharmaceuticals, Inc., published Jul. 20, 1988; Aoyagi, Miyata, Nanbo, Kojima, Matsuzaki, Ishizuka, Takeuchi & Umezawa, "Biological Activities of Leupeptins," *The Journal of Antibiotics*, Vol. XXII, No. 11 (Nov. 1969), pp. 558–568; Bajusz, Barabas, Tolnay, Szell & Bagdy, "Inhibition of Thrombin and Trypsin by Tripeptide Aldehydes," *Int. J. Peptide Protein Res.*, Vol. 12 (1978), pp. 217–221; Gaal, Bacsy & Rappay, "Cationic Ferritin Uptake by Cultured Anterior Pituitary Cells Treated with the Proteinase Inhibitor, BOC-DPhe-Phe-Lys-H," *Histochemistry*, Vol. 88 (1988), pp. 401–406; Makara, Rappay, Garamvolgyi, Nagy, Danko & Bajusz, "The Tripeptide Aldehyde, Boc-DPhe-Phe-Lysinal, is a Novel $Ca^{2+}$ Channel Inhibitor in Pituitary Cells," *European Journal of Pharmacology*, Vol. 151 (1988), pp. 147–149; Nagy, Makara, Horvath, Rappay, Kurcz & Bajusz, "Tripeptide Aldehyde Protease Inhibitors May Depress in Vitro Prolactin and Growth Hormone Release," *Endocrinology*, Vol. 116, No. 4 (1895), pp. 1426–1432; Rappay, Makara, Bajusz & Nagy, "Various Proteinase Inhibitors Decrease Prolactin and Growth Hormone Release by Anterior Pituitary Cells," *Life Sciences*, Vol. 36 (1985), pp. 549–555.

It is an object of the subject invention to provide novel difluoro pentapeptide derivatives which are useful as anti-inflammatory agents.

It is a further object of the subject invention to provide novel difluoro pentapeptide derivatives which reduce bone resorption and/or heterotopic bone formation associated with rheumatoid arthritis.

It is also an object of the subject invention to provide novel pharmaceutical compositions comprising certain difluoro pentapeptide derivatives.

It is also an object of the subject invention to provide methods for treating diseases characterized by inflammation using the subject compounds.

SUMMARY OF THE INVENTION

The subject invention involves anti-inflammatory compounds having the following structure:

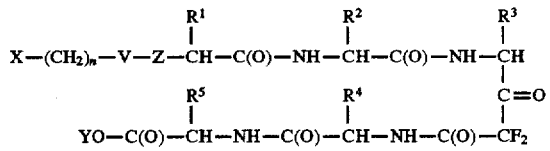

wherein:

(a) —X is selected from the group consisting of cyclic alkyl having from 4 to about 15 carbon atoms; branched alkyl, with at least two branches, having from 6 to about 15 carbon atoms; and arylalkyl having from 6 to about 15 carbon atoms;

(b) n is an integer from 0 to about 2;

(c) —V— is selected from the group consisting of —OC(O)—, —N(Q)C(O)—, —N(Q)C(S)—, —C(O)—, —SO$_2$— and —P(O)(OH)—;

(d) —Q is hydrogen; or straight or branched chain alkyl, saturated or unsaturated with 1 or 2 double bonds, having from 1 to about 6 carbon atoms; or —Q and —X are covalently linked forming a cyclic moiety which includes the nitrogen to which —Q is bonded and from about 5 to about 20 carbon atoms;

(e) Z is —O— or —NH—; when V is —OC(O)—, —Z— is —NH—;

(f) —R$^1$ is selected from the group consisting of straight or branched alkyl, saturated or unsaturated with 1 or 2 double bonds, having from I to about 6 carbon atoms; cyclic alkyl, saturated or unsaturated with 1 or 2 double bonds, having from 3 to about 10 carbon atoms; and arylalkyl wherein the aliphatic portion is saturated and has 1 or 2 carbon atoms; and the carbon atom bonded to —R$^1$ is in either D or L configuration;

(g) —R$^2$ is selected from the group consisting of straight or branched alkyl, saturated or unsaturated with 1 or 2 double bonds, having from 1 to about 6 carbon atoms; cyclic alkyl, saturated or unsaturated with 1 or 2 double bonds, having from 3 to about 10 carbon atoms; and arylalkyl wherein the aliphatic portion is saturated and has 1 or 2 carbon atoms; and the carbon atom bonded to —R$^2$ is in L configuration;

(h) —R$^3$ is —(CH$_2$)$_m$—A—NH$_2$ or —(CH$_2$)$_m$—A—B—C(NH$_2$)=NH wherein m is an integer from 1 to about 6, —A— is a covalent bond or p-phenyl or p-cyclohexyl, and —B— is a covalent bond or —NH—; and the carbon atom bonded to —R$^3$ is in L configuration;

(i) —R$^4$ is selected from the group consisting of straight or branched alkyl, saturated or unsaturated with 1 or 2 double bonds, having from 1 to about 6 carbon atoms;

cyclic alkyl, saturated or unsaturated with 1 or 2 double bonds, having from 3 to about 10 carbon atoms; and arylalkyl wherein the aliphatic portion is saturated and has 1 or 2 carbon atoms; and the carbon atom bonded to —R⁴ is in L configuration;

(j) —R⁵ is —(CH₂)ₘ—A—NH₂ or —(CH₂)ₘ—A—B—C(NH₂)=NH wherein m is an integer from 1 to about 6. —A— is a covalent bond or p-phenyl or p-cyclohexyl, and —B— is a covalent bond or —NH—; and the carbon atom bonded to —R⁵ is in D or L configuration; and (k) —Y is hydrogen or methyl.

The subject invention also involves pharmaceutical compositions comprising the above compounds, and methods for treating inflammation or pain using such compounds and compositions.

DETAILED DESCRIPTION OF THE INVENTION

The term "alkyl," as used herein, unless otherwise indicated, means carbon-containing chains which may be straight, branched or cyclic; which may be saturated or unsaturated; and which may be unsubstituted or substituted. As used herein, "cyclic alkyl" may have all or only a portion of the total number of carbon atoms indicated as being in the alkyl group in the cyclic ring itself. Cyclic alkyl includes monocycloalkyl, bicycloalkyl and/or tricycloalkyl.

Preferred alkyl are as noted in this paragraph unless provided otherwise in particular instances. Preferred alkyl are saturated. Preferred alkyl are unsubstituted. Preferred alkyl substituents are selected from halo, amino, hydroxy, alkoxy, cyano, nitro, aryl and trifluoromethyl. As used herein, "alkoxy" is —O-alkyl. It is preferred that substituted alkyl be mono-, di- or trisubstituted, especially monosubstituted.

The term "aryl," as used herein, unless otherwise specified, means aryl rings which may be unsubstituted or substituted. Preferred aryl is as noted in this paragraph, unless provided otherwise in particular instances. Preferred aryl are phenyl and naphthyl, especially phenyl. Preferred aryl are mono-, di-, tri- or unsubstituted; more preferred aryl are monosubstituted or unsubstituted, especially unsubstituted. Preferred aryl substituents include alkyl, halo, amino, hydroxy, alkoxy, cyano, nitro and trifluoromethyl.

The term "arylalkyl," as used herein, means alkyl substituted with aryl. A preferred arylalkyl is arylmethyl.

The term "aliphatic" as used herein, means open-chain carbon-containing portions of arylalkyls.

The following abbreviations are used herein. Abbreviations for amino acids may refer to the amino acid itself, or more often to an amino acid moiety that is part of a peptide or peptide derivative structure.

Arg Arginyl
Orn Ornithyl
Leu Leucyl
Gly Glycyl
t-Bug t-Butylglycyl
Phe Phenylalanyl
Adoc Adamantyloxycarbonyl
Z Benzyloxycarbonyl
Boc t-Butyloxycarbonyl
DECP Diethylcyanophosphonate
Me Methyl
Et Ethyl
TEA Triethylamine
DMF Dimethylformamide
TFA Trifluoroacetate
ipa Isopropanol
Bn Benzyl
Lys Lysyl
Ac Acetyl
TLC Thin Layer Chromatography
TSA Toluenesulfonic acid
THF Tetrahydrofuran
HOBt Hydroxybenzotriazole
DCC Dicyclohexylcarbodiimide
DIPEA N,N-Diisopropylethylamine
Chg Cyclohexylglycyl
Cha Cyclohexylalanyl
Nal Naphthylalanyl
Trp Tryptophyl
Adg Adamantylglycyl
pGphe p-Guanidinophenylalanyl
3,5-Dmadoc 3,5-Dimethyladamantyloxycarbonyl
eBroc endo-Bornyloxycarbonyl
Noc Naphthyloxycarbonyl
Moc Menthyloxycarbonyl
Ad Adamantoyl
Fmoc Fluorenylmethoxycarbonyl
Ada Adamantaneacetyl
Adac Adamantylaminocarbonyl
Mnoc Morpholinyl
Norad Noradamantoyl
Hadoc Homoadamantyloxycarbonyl
Foc Fenchyloxycarbonyl
Imoc Isomenthyloxycarbonyl
Ipoc Isopinocamphanyloxycarbonyl
AC acetyl
DMF dimethylformamide
HPLC high pressure liquid chromatography The novel anti-inflammatory compounds of the subject invention are those having the following chemical structure:

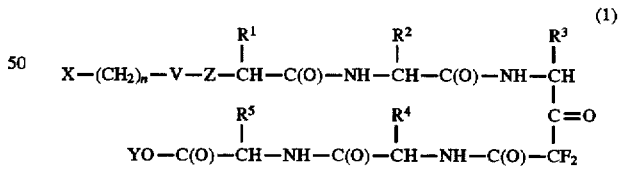

(1)

In Structure (1), n is an integer of from 0 to about 2; n is preferably 0 or 1.

In Structure (1), —R¹ is selected from the group consisting of straight or branched alkyl, saturated or unsaturated with 1 or 2 double bonds, having from 1 to about 6, carbon atoms; cyclic alkyl, saturated or unsaturated with 1 or 2 double bonds, having from 3 to about 10 carbon atoms; and arylalkyl, the aliphatic portion being saturated and having I or 2 carbon atoms. Preferred —R¹ is saturated alkyl. Preferred alkyl are unsubstituted, or are arylalkyl, especially benzyl and naphthal. Preferred cyclic alkyl are cyclic C3–C8 (more preferably C₅–C₆) methyl or adamantylmethyl. Preferred —$R^1$ is hydrophobic, preferably with the hydrophobicity concentrated close to the carbon atom to which —$R^1$ is bonded. Specific examples of preferred —$R^1$ include t-butyl, 1,1-dimethylpropyl, i-propyl, i-butyl, s-butyl, neopentyl, cyclohexyl, cyclohexylmethyl, adamantyl, adamantylmethyl, benzyl, naphthal; most preferred —$R^1$ is t-butyl.

In Structure (1), the carbon to which —$R^1$ is bonded is in either D or L, preferably D, configuration. The structure —Z—CH($R^1$)—C(O)— is an amino acid moiety (hereinafter —$AA^1$—) when —Z— is —NH; preferred amino acid moieties for —$AA^1$— include t-Bug, Val, Ile, Leu, Chg, Cha, Phe, Nal, Trp and Adg; more preferred are t-Bug, Val and Ile; most preferred —$AA^1$— is t-Bug.

In Structure (1), —$R^2$ is selected from the group consisting of straight or branched alkyl, saturated or unsaturated with 1 or 2 double bonds, having from 1 to about 6 carbon atoms; cyclic alkyl, saturated or unsaturated with 1 or 2 double bonds, having from 3 to about 10 carbon atoms; and arylalkyl, the aliphatic portion being saturated and having 1 or 2 carbon atoms. Preferred branched or cyclic alkyl are saturated. Preferred branched or cyclic alkyl are unsubstituted. Preferred branched alkyl have from 3 to 5 carbon atoms; most preferred branched alkyl is i-butyl. Preferred cyclic alkyl have a $C_3$–$C_7$, more preferably $C_5$–$C_6$, cyclic ring bonded to a methylene, ethylene or n-propylene (preferably methylene or ethylene, more preferably methylene) which is bonded to the carbon atom in Structure (1) to which —$R^2$ is bonded. Preferred arylalkyl are benzyl, p-hydroxybenzyl and naphthal. More preferred —$R^2$ is selected from i-propyl, i-butyl, s-butyl, cyclohexylmethyl, benzyl and naphthal; most preferred is benzyl.

In Structure (1), the carbon atom to which —$R^2$ is bonded is in D or L configuration. The structure —NH—CH($R^2$)—C(O)— is an amino acid moiety (hereinafter —$AA^2$—); preferred amino acid moieties for —$AA^2$— include Phe, Nal, Cha, Leu and Ile; most preferred —$AA^2$— is Phe.

In Structure (1), —$R^3$ is —$(CH_2)_m$—A—$NH_2$ or —$(CH_2)_m$—A—B—C($NH_2$)=NH, wherein m is an integer of from 1 to about 6, —A— is a covalent bond, p-phenyl or p-cyclohexyl, and —B— is a covalent bond or —NH—. When —A— is a covalent bond, m is preferably 2–5, more preferably 2–4, more preferably still 3 or 4. When —A— is p-phenyl or p-cyclohexyl, m is preferably 1–4, more preferably 1–3, more preferably still 1. —A—is preferably a covalent bond. —B— is preferably —NH—. More preferred —$R^3$ is 3-guanidino-n-propyl or 4-amino-n-butyl.

In Structure (1), the carbon to which —$R^3$ is bonded is in D or L configuration, preferably in L configuration. The structure —NH—(CH($R^3$)—C(O)— is an amino acid moiety (hereinafter —$AA^3$—); preferred amino acid moieties for —$AA^3$— include Arg, Lys, homo-Arg, p-amidino-phe, p-amino-phe and p-Gphe; most preferred —$AA^3$— is Lys.

In Structure (1), —$R^4$ is selected from the group consisting of straight or branched alkyl, saturated or unsaturated with 1 or 2 double bonds, having from 1 to about 6 carbon atoms; cyclic alkyl, saturated or unsaturated with 1 or 2 double bonds, having from 3 to about 10 carbon atoms; and arylalkyl, the aliphatic portion being saturated and having 1 or 2 carbon atoms. Preferred branched or cyclic alkyl are saturated and unsubstituted. Preferred branched alkyl have from 3 to 5 carbon atoms; most preferred branched alkyl is i-butyl. Preferred cyclic alkyl have a $C_3$–$C_7$, more preferably $C_5$–$C_6$ cyclic ring bonded to a methylene, ethylene or n-propylene (preferably methylene or ethylene, more preferably methylene) which is bonded to the carbon atom in Structure (1) to which —$R^4$ is bonded. Preferred arylalkyl are benzyl, p-hydroxybenzyl and naphthal. More preferred —$R^4$ is selected from i-propyl, i-butyl, s-butyl, cyclohexylmethyl, benzyl and naphthal; most preferred is benzyl.

In Structure (1), the carbon atom to which —$R^4$ is bonded is in D or L configuration. The structure —NH—CH($R^4$)—C(O)— is an amino acid moiety (hereinafter —$M^4$—); preferred amino acid moieties for —$AA^4$— include Phe, Nal, Cha, Leu and Ile; most preferred —$AA^4$— is Leu.

In Structure (1), —$R^5$ is —$(CH_2)_m$—A—$NH_2$ or —$(CH_2)_m$—A—B—C($NH_2$)=NH, wherein m is an integer from 1 to about 6, —A— is a covalent bond, p-phenyl or p-cyclohexyl, and —B— is a covalent bond or —NH—. When —A— is a covalent bond, m is preferably 2–5, more preferably 2–4, more preferably still 3 or 4. When —A— is p-phenyl or p-cyclohexyl, m is preferably 1–4, more preferably 1–3, more preferably still 1. —A— is preferably a covalent bond. —B— is preferably —NH—. More preferred —$R^5$ is 3-guanidino-n-propyl or 4-amino-n-butyl.

In Structure (1), the carbon to which —$R^5$ is bonded is in D or L configuration, preferably in L configuration. The structure —NH—CH($R^5$)—C(O)— is an amino acid moiety (hereinafter —$AA^5$); preferred amino acid moieties for —$AA^5$ include Arg, homo-Arg, Lys, p-amidino-Phe, p-amino-Phe and p-Gphe; most preferred —$AA^5$—is Arg.

In Structure (1), —Y is hydrogen or methyl.

In Structure (1), —Z— is —O— or —NH—. Preferred —Z— is —NH—.

In Structure (1), —V— is selected from —OC(O)—, —N(Q)C(O)—, —N(Q)C(S)—, —C(O)—, —$SO_2$— and —P(O)(OH)—. Preferred —V— is selected from —OC(O)—, —N(Q)C(O)—, —N(Q)C(S)—, and —C(O)—. More preferred —V— is —OC(O)— or —N(Q)C(O)—. Most preferred —V— is —OC(O)—. When —V— is —OC(O)—, —Z— is —NH—.

In Structure (1), —X is selected from cyclic alkyl, having from 4 to about 15 carbon atoms; branched alkyl having from 6 to about 15 carbon atoms and at least 2 branches; and aryl, having from 6 to about 15 carbon atoms. Preferred —X has from 6 to 12 carbon atoms; more preferred —X has from 8 to 10 carbon atoms. Preferred alkyl portions of —X are saturated. Preferred —X is unsubstituted, or substituted with unsubstituted alkyl or aryl. Preferred cyclic alkyl are monocycloalkyl, bicycloalkyl, and tricycloalkyl, more preferred are bicycloalkyl and tricycloalkyl, especially tricycloalkyl. Preferred cycloalkyl have 5 or 6 carbon atoms, more preferably 6 carbon atoms, in each cyclic ring. A highly preferred —X is adamantyl. Preferred aryl —X are fluorenyl, naphthyl and phenyl, unsubstituted or substituted with alkyl. Particularly preferred aryl —X include naphthyl and fluorenyl. When —X is aryl or cyclic alkyl, n is preferably 1.

In Structure (1) when —V— is —N(Q)C(O)— or —N(Q)C(S)—, —Q is selected from hydrogen; straight or branched alkyl, saturated or unsaturated with 1 or 2 double bonds, having from 1 to about 6 carbon atoms; or —Q and —X are covalently linked forming a cyclic moiety which includes the nitrogen to which —Q is bonded and from about 5 to about 20 carbon atoms. Preferred —Q—X— has from 6 to 15 carbon atoms; more preferred —Q—X— has from 8 to 12 carbon atoms. Preferred —Q—X— is unsubstituted or substituted with unsubstituted alkyl or aryl. Preferred cyclic

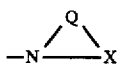

is monocyclic, bicyclic or tricyclic; more preferred is monocyclic. Most preferred —Q is hydrogen.

In Structure (1), preferred X—(CH$_2$)$_n$—V— (hereinafter X'—) include Adoc, Ad, Fmoc, Ada, Adac, Mnoc, Norad, Hadoc, Foc, Imoc, Ipoc, 3,5-Dmadoc, eBroc, Noc and Moc; more preferred X' is Adoc, Ipoc and eBroc; most preferred —X' is Adoc.

Preferred anti-inflammatory compounds of the subject invention include pharmaceutically-acceptable salts of the above compounds. Particularly preferred salts include salts of addition formed between a strong acid and the above compounds. Particularly preferred are such salts of addition where either —R$^3$ or —R$^5$, or both, are protonated, resulting in a positive charge on the —R$^3$ and R$^5$ moieties. Preferred compounds of the subject invention are often associated with one or more molecules of water in the form of hydrates.

Preferred anti-inflammatory compounds of the subject invention include the following compounds:

Adoc-D-tBug-Phe-Lys—C(O)CF$_2$C(O)—Leu-Arg-OMe
Adoc-D-tBug-Phe-Lys—C(O)CF$_2$C(O)—Gly-Arg-OMe
Adoc-D-tBug-Phe-Lys—C(O)CF$_2$C(O)—D-Phe-Arg-OMe
Adoc-D-tBug-Phe-Lys—C(O)CF$_2$C(O)—Leu-D-Arg-OMe
Mnoc-D-Phe-Phe-Arg—C(O)—CF$_2$C(O)—Leu-Lys-OMe
eBroc-D-t-Bug-Phe-pGphe—C(O)CF$_2$C(O)—Ala-Arg-OMe
Ipoc-D—Nal-Phe-Arg—C(O)CF$_2$C(O)—Gly-Arg-OMe
Adoc-D-Phe-Phe-Lys—C(O)CF$_2$C(O)—Leu-Arg-OH
Noc-D-t-Bug-Phe-Lys—C(O)CF$_2$C(O)—Ala-Lys-OMe

Pharmaceutical Compositions

Pharmaceutical compositions of the subject invention comprise a safe and effective amount of a difluoro pentapeptide derivative as defined hereinabove and a pharmaceutically-acceptable carrier. Such compositions typically comprise from about 0.1% to about 95% by weight of the difluoro pentapeptide derivative, preferably from about 1% to about 90% and more preferably from about 5% to about 75%.

The term "pharmaceutically-acceptable carrier," as used herein, means one or more compatible solid or liquid filler diluents or encapsulating substances which are suitable for administration to a human or lower animal. The term "compatible," as used herein, means that the components of the pharmaceutical compositions are capable of being commingled with the difluoro pentapeptide derivative of the subject invention, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars, such as lactose, glucose and sucrose; starches, such as cornstarch and potato starch; cellulose and its derivatives, such as sodium carboxy-methylcellulose, ethylcellulose and cellulose acetate; powdered tragacanth; malt; gelatins; talc; stearic acid; magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; alginic acid; pyrogen-free water; isotonic saline; phosphate buffer solutions; cocoa butter (suppository base); emulsifiers, such as Tweens®; wetting agents and lubricants, such as sodium lauryl sulfate; coloring agents; flavoring agents; stabilizers; antioxidants; preservatives; as well as other non-toxic compatible substances used in pharmaceutical formulations. Other compatible pharmaceutical additives and actives may be included in the pharmaceutically-acceptable carrier for use in the compositions of the subject invention.

The pharmaceutically-acceptable carrier employed in conjunction with the difluoro pentapeptide derivative of the subject invention is used at a concentration sufficient to provide a practical size to dosage relationship. The pharmaceutically-acceptable carrier, in total, typically comprises from about 5% to about 99.9% by weight of the pharmaceutical compositions of the subject invention, preferably from about 10% to about 99%, and more preferably from about 25% to about 95%.

Total single dosages of the difluoro pentapeptide derivatives of the subject invention in pharmaceutical compositions are generally from about 1 mg to about 1000 mg, preferably from about 50 mg to about 800 mg, more preferably from about 100 mg to about 500 mg.

The choice of a pharmaceutically-acceptable carrier to be used in conjunction with the difluoro pentapeptide derivatives of the subject invention is determined by the way the active is to be administered. Preferred modes of administering the actives of the subject invention are by injection, ingestion, inhalation and topically.

Methods and materials for manufacturing injectables can be found in *Remington's Pharmaceutical Sciences*, 17th ed., 1985, Chapter 85, p. 1518, the disclosures of which are incorporated herein by reference in their entirety. Generally, three types of injectable dosage forms are preferred: (1) aqueous solutions, (2) non-aqueous solutions; and (3) emulsions. Injectable dosage forms typically contain from about 0.001 mg/ml to about 10 mg/ml, preferably from about 0.4 mg/ml to about 0.6 mg/ml, of a compound of the subject invention. Preferred injectable dosage compositions of the subject invention include sterile aqueous solutions or emulsions of pH from about 3 to about 8 (more preferably of pH from about 4 to about 6).

Preferred pharmaceutical carriers in which the difluoro pentapeptide derivatives of the subject invention can be administered by ingestion are proteinoid microcapsules disclosed in the following patents: U.S. Pat. No. 4,895,725 issued to Kantor, Steiner & Pack on Jan. 23, 1990; U.S. Pat. No. 4,925,673 issued to Steiner & Rosen on May 15, 1990; U.S. Pat. No. 4,976,968 issued to Steiner on Dec. 11, 1990; and U.S. Pat. No. 4,983,402 issued to Steiner on Jan. 8, 1991; all four patents are hereby incorporated in their entirety by reference.

Methods for Producing Anti-inflammatory Activity and Analgesia

The subject invention also encompasses methods of producing anti-inflammatory activity and/or analgesia in humans or lower animals through administering, to the human or lower animal in need of such treatment, a safe and effective amount of a difluoro pentapeptide derivative of the subject invention. The amount can be given in a single dose or multiple doses repeatedly over the course of the treatment. While dosages higher than those described herein are effective to reduce inflammation and produce analgesia, care must be taken in some individuals to prevent adverse side effects. The difluoro pentapeptide derivatives and compositions of the subject invention can be used to reduce inflammation in various disorders at the deeper structures, muscles, tendons, bursa and joints associated with disease and trauma, to treat and prevent pain.

The preferred modes of administering the difluoro pentapeptide derivatives of the subject invention are by injection, ingestion, inhalation-and topically. Specific modes of administration include, without limitation, oral ingestion; injection, such as intramuscular, intravenous, intraperitoneal, intradermal and subcutaneous; inhalation; and topically, such as transdermally, orally, mucosally and sublingually.

The term "safe and effective amount," as used herein, means an amount of a difluoro pentapeptide derivative or composition high enough to significantly positively modify the condition to be treated, but low enough to avoid serious side effects (at a reasonable benefit/risk ratio), within the scope of sound medical judgement. A safe and effective amount of a difluoro pentapeptide derivative or composition will vary with the particular condition being treated, the age and physical condition of the patient being treated, the severity of the condition, the duration of the treatment, the nature of concurrent therapy, the specific active employed, the particular pharmaceutically-acceptable carrier utilized, and like factors within the knowledge and expertise of the attending physician.

Preferred daily dosages of the difluoro pentapeptide derivatives of the subject invention range from about 0.1 mg/kg of body weight to about 500 mg/kg of body weight, more preferably from about 1 mg/kg to about 100 mg/kg, still more preferably from about 2 mg/kg to about 50 mg/kg. From 1 to about 4 single dosages per day may be administered, more preferably from about 2 to about 3 single dosages per day. Preferred amounts of the difluoro pentapeptide derivatives administered by injection are from about 0.1 mg/kg/day to about 50 mg/kg/day, more preferably from about 1 mg/kg/day to about 10 mg/kg/day. Preferred amounts of the difluoro pentapeptide derivatives administered by oral ingestion are from about 1 mg/kg/day to about 500 mg/kg/day, more preferably from about 5 mg/kg/day to about 100 mg/kg/day. Preferred amounts of the difluoro pentapeptide derivatives administered by inhalation are from about 0.1 mg/kg/day to about 500 mg/kg/day, more preferably from about 5 mg/kg/day to about 100 mg/kg/day. Preferred amounts of the difluoro pentapeptide derivatives administered topically are from about 1 mg/kg/day to about 500 mg/kg/day, more preferably from about 50 mg/kg/day to about 250 mg/kg/day.

Methods for Synthesizing the Compounds

The following non-limiting schemes and examples demonstrates methods of synthesizing difluoro pentapeptide derivatives of the subject invention.

I. Synthesis of Adoc-D-t-Bug-Phe-Lys-C(O)-$CF_2$-C(O)-Leu-Arg-OMe

Adoc-D-t-Bug-OH

To a solution of 48.8 g (0.370M) of D-t-butylglycine in 371 ml of 1N NaOH and 159 ml of dioxane at 0 C. was added 33.9 g (0.40M) of $NaHCO_3$ followed by the dropwise addition of a solution of 80.0 g (0.40M) of adamantyl fluoroformate in 371 ml of dioxane over 3 h. The mixture is stirred at this temperature for 0.5 h and the cooling bath removed. The solution is stirred for 3 h and the pH adjusted to 10 with 1N NaOH. This solution is extracted with EtOAc and the remaining aqueous phase acidified to pH=3. This acidic solution is extracted with EtOAc, dried and the solvent removed to afford 118 g of product that is homogeneous by TLC (94/5/1—$CH_2Cl_2$/ipa/AcOH), Rf=0.90.

Adoc-D-t-Bug-Phe-OBn

To a solution of 115 g (0.37M) of Adoc-D-t-Bug-OH and L-Phe-OBn.pTSA (0.36M) in 1 L $CH_2Cl_2$ is added 74.6 g (0.74M) of TEA followed by the addition of 60.8 g (0.37 M) of DECP and the resulting solution is stirred overnight. The solvent is removed and the product redissolved in EtOAc and washed successively with brine, 0.4N HCl, and saturated $NaHCO_3$. The solution is dried and the solvent removed. The residue is chromatographed on silica to afford 186 g of product. TLC (85/15—hexane/ETOAc—Rf =0.40.

Adoc-D-tBug-Phe-OH (1)

To a dry flask under $N_2$ is added 34.0 g 5% Pd on carbon. The flask is cooled to −78° C. and 200 ml of dry degassed MeOH is added. To this slurry is added 8.8 ml of formic acid (88%) and this is followed by the addition of a mixture of 36.0 g of Adoc-D-t-Bug-Phe-OBn (0.066M) in 100 ml of MeOH and 4.4 ml of formic acid. The cooling bath is removed and the slurry stirred for 2 h. At this time an additional 200 ml of 4.4% formic acid in MeOH is added and the slurry stirred over-night. The mixture is filtered through glass fiber filter paper under $N_2$. The filtrate is refiltered through a bed of Celite to remove all traces of catalyst. Removal of the solvent yields 17.3 g of product.

α-boc, Σ-Z-Lys-C(OH)-$CF_2$-C(O)-OEt (3)

To a solution of 79.2 g (1.21M) of activated zinc in 0.600 L THF is added 2.36 g of ethyl bromodifluoroacetate and the solution brought to reflux. As soon as reflux begins a mixture of 236 g (1.16M) of ethyl bromodifluoroacetate and 176 g (0.485M) of (2) in 1.80 L of THF is added dropwise. For the synthesis of (2), see Burkhart, J., N. Peet and P. Bey, "A Novel Method for the Preparation of Peptidyl α-Keto Esters," *Tetrahedron Letters*, Vol. 31, No. 10, pp. 1385–1388 (1990). The solution is refluxed for 1 h, cooled and quenched with saturated $KHSO_4$. The quenched product is diluted with EtOAc and washed successively with saturated $KHSO_4$, saturated $NaHCO_3$ and brine. This sequence is followed by drying with $MgSO_4$ and removal of solvent. The residue is chromatographed on silica to afford 68.0 g of pure product. Rf=0.20 75/25 hexane/EtOAc.

α-Boc, Σ-Z-Lys-C(OH)-$CF_2$-C(O)-ONa (4)

To a solution of 1.00 g (0.002M) of (3) in 10 ml of MeOH is added 2 ml of 1N NaOH and the solution stirred at room temperature for 5 h and the solvent is removed. The residue is dissolved in a small amount of water and the milky solution extracted with ether. The water is removed from the aqueous phase and the residue thoroughly dried by placing on the vacuum pump for 24 h. Recovered 0.069 g of product is recovered.

α-Boc, Σ-Lys-C(OH)-$CF_2$-C(O)-Leu-Arg($N_2$)-OMe (5)

To a solution of 0.500 g (1.03 mmol) of (4) and 0.470 g (1.26 mmol) of Leu-Arg($NO_2$)—OMe.HCl in 30 ml of DMF is added 0.019 g (1.26 mmol) of HOBt in one portion. This addition is followed by the drop-wise addition of 0.260 g (1.26 mmol) of DCC in 3 ml DMF. Finally, 0.003 ml of DIPEA is added and the solution stirred for 48 h. The DMF is removed in vacuo and the residue dissolved in EtOAc. The solution is transferred to a separatory funnel and washed with 0.1N HCl, saturated $NaHCO_3$, and brine. The ethyl acetate layer is dried with $MgSO_4$, filtered and the solvent removed. The residue is chromatographed on silica to afford 0.420 g of product. Rf=0.68—90/10 $CH_2Cl_2$/MeOH.

Σ-Z-Lys—C(OH)-$CF_2$-C(O)-Leu-Arg($NO_2$)-OMe.HCl

To a solution of (5) (17.3 g, 0.022M) in 200 ml of dioxane is added 66.8 ml (0.220 m) of 3.3M HCl in dioxane and the mixture stirred for 1 h. At this time an additional 5 ml of 3.3M HCl in dioxane is added and the solution stirred an additional 0.25 h. The solvent is removed and the residue placed on the vacuum pump. The solid residue is triturated with ether under $N_2$ and filtered. Recovered 16.0 g of white solid.

Adoc-D-t-Bug-Phe-Lys(Z)-C(OH)-CF$_2$-C(O)—Leu-Arg(NO$_2$)-OMe (6)

To a solution of 16.0 g of the residue from the previous reaction (0.022M) and 11.1 g of (1) (0.024M) in 300 ml of $CH_2Cl_2$ is added 6.69 ml (0.048M) of TEA dropwise followed by the dropwise addition of 3.64 ml (0.024M) of DECP. The solution is stirred overnight and the solvent removed. The residue is dissolved in EtOAc and washed successively with 0.1N HCl, saturated NaHCO$_3$, and brine. The solution is dried and the solvent removed to afford 26.6 g that is chromatographed on silica to afford 12.7 g of pure product. Rf=0.85, 90/10—$CH_2Cl_2$/MeOH.

Adoc-D-t-Bug-Phe-Lys(Z)-C(O)CF$_2$C(O)-Leu-Arg(NO$_2$)-OMe

To a slurry of 14.3 g (0.034M) of Dess-Martin periodinane in 1.15 L of $CH_2Cl_2$ is added 0.910 ml of dry pyridine, followed by the dropwise addition of 12.7 g (0.011M) of (6) in 2.3 L of $CH_2Cl_2$. For the preparation of Dess-Martin periodidinane, see Dess, D., and J. Martin, *Journal of Organic Chemistry*, Vol. 48 pp. 4155–4156 (1983). The slurry is stirred for 2 h and 58.7 g (0.24M) of $Na_2S_2O_4$ in saturated NaHCO$_3$ added and the resulting solution stirred for 0.5 h. The phases are separated and the aqueous phase extracted with ethyl acetate. The combined organic phases are dried and the solvent removed to give 13.9 g of product that is used in the next reaction without purification. (Rf 0.30— 95/5 $CH_2Cl_2$/MeOH).

Adoc-D-t-Bug-Phe-Lys-C(O)CF$_2$C(O)-Leu-Arg-OMe (7)

To a solution of 13.4 g (0.012M) of the residue from the previous reaction in 200 ml of dry DMF is added 6 g of palladium black and the resulting slurry degassed for 0.5 h. To this slurry is added 8 ml of 3.3M HCl in dioxane. The reaction is placed on the Paar shaker and hydrogenated for 6 h. The slurry is filtered through Celite and the solvent removed. The residue is chromatographed on reverse phase HPLC (CH$_3$CN/H$_2$O) to afford 6.5 g product.

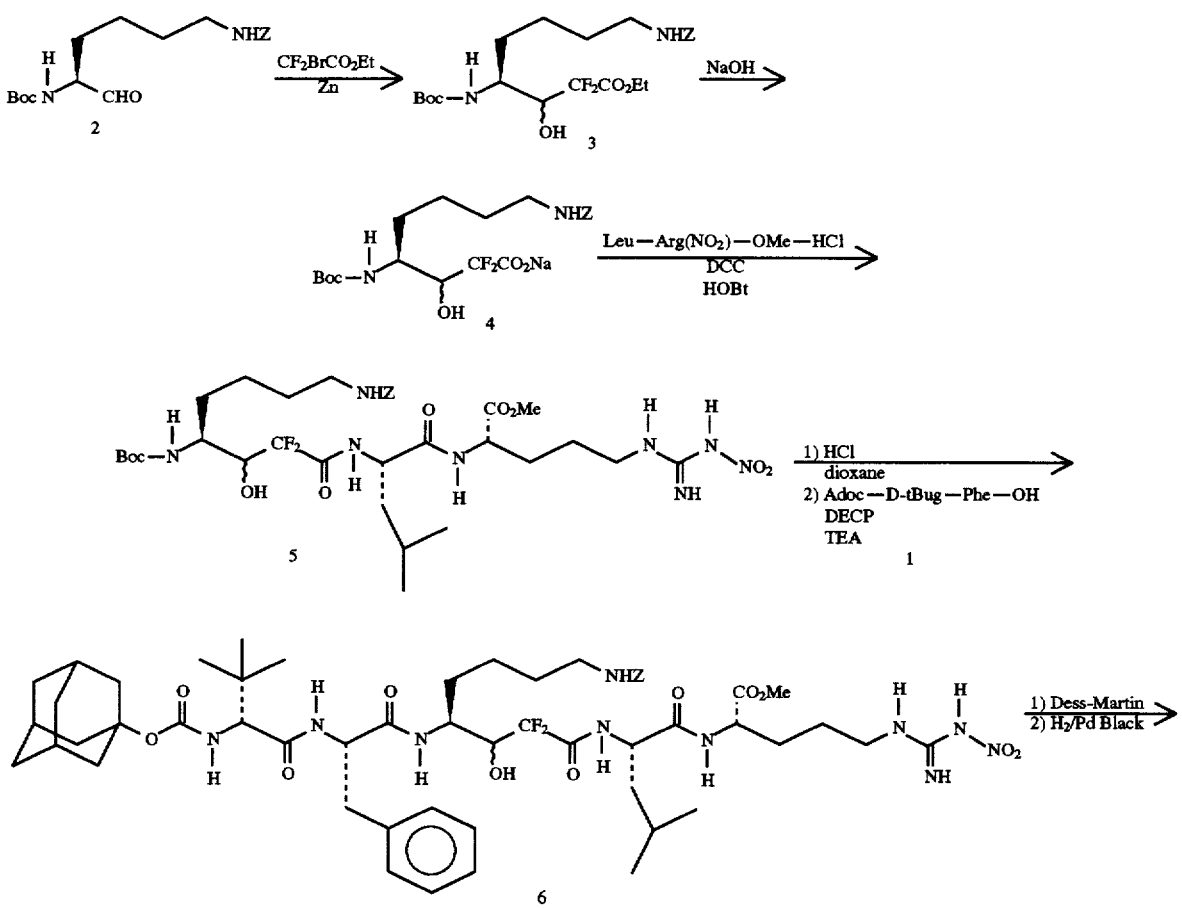

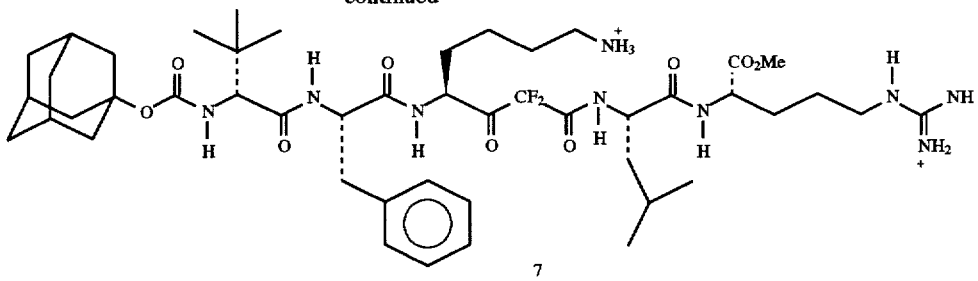

7

II. Synthesis of Adoc-D-t-BuQ-Phe-Arg-C(O)-CF₂-C(O)—Ala-Arg-OMe

Adoc-D-t-Bug-OH

To a solution of 48.8 g (0.370M) of D-t-butylglycine in 371 ml of 1N NaOH and 159 ml of dioxane at 0° C. is added 33.9 g (0.40M) of adamantyl fluoroformate in 371 ml of dioxane over 3 hours. The mixture is stirred at this temperature for 0.5 hours and the cooling bath is removed. The solution is stirred for 3 hours and the pH adjusted to 10 with 1N NaOH. This solution is extracted with EtOAc and the remaining aqueous phase acidified to pH=3. This acidic solution is extracted with EtOAc, dried and the solvent is removed to afford 118 g of product that is homogeneous by TLC (94/5/1—CH₂Cl₂/i-pa/AcOH), Rf=0.90.

Adoc-D-t-Bug-Phe-OBn

To a solution of 115 g (0.37M) of Adoc-D-t-But-OH and L-Phe-OBn.pTSA (0.36M) in 1L CH₂Cl₂ is added 74.6 g (0.74M) of TEA followed by the addition of 60.8 g (0.37M) of DECP and the resulting solution is stirred overnight. The solvent is removed and the product is redissolved in EtOAc and washed successively with brine, 0.4N NCl, and saturated NaHCO₃. The solution is dried and the solvent is removed. The residue is chromatographed on silica to afford 186 g of product. TLC (85/15—hexane/EtOAc)—Rf=0.40.

Adoc-D-t-BuQ-Phe-OH (1)

To a dry flask under N₂ is added 34.0 g 5% Pd on carbon. The flask is cooled to –78° C. and 200 ml of dry degassed MeOH is added. To this slurry is added 8.8 ml of formic acid (88%) and this is followed by the addition of a mixture of 36.0 g of Adoc-D-t-Bug-Phe-OBn (0.066M) in 100 ml of MeOH and 4.4 ml of formic acid. The cooling bath is removed and the slurry is stirred for 2 hours. At this time an additional 200 ml of 4.4% formic acid in MeOH is added and the slurry is stirred overnight. The mixture is filtered through glass fiber filter paper under N₂. The filtrate is refiltered through a bed of Celite to remove all traces of catalyst. Removal of the solvent yields 17.3 g of product.

α-Boc, Σ-Z-Lys-C(OH)-CF₂-C(O)-OEt (3)

To a solution of 79.2 g (1.21M) of activated zinc in 0.600 L THF is added 2.36 g of ethyl bromodifluoroacetate and the solution is brought to reflux. As soon as reflux begins, a mixture of 236 g (1.16M) of ethyl bromodifluoroacetate and 176 g (0.485M) of Z in 1.80 L of THF is added dropwise. The solution is refluxed for 1 hour, cooled and quenched with saturated KHSO₄. The quenched product is diluted with EtOAc and washed successively with saturated KHSO₄, saturated NaHCO3 and brine. This sequence is followed by drying with MgSO₄ and removal of solvent. The residue is chromatographed on silica to afford 68.0 g of pure product. Rf=0.20 75/25 hexane/EtOAc.

α-Boc, Σ-Z-Lys-C(OH)-CF₂-C(O)-ONa (4)

To a solution of 1.00 g (0.002M) of 3 in 10 ml of MeOH is added 2 ml of 1N NaOH. The solution is stirred at room temperature for 5 hours and the solvent is removed. The residue is dissolved in a small amount of water and the milky solution is extracted with ether. The water is removed from the aqueous phase and the residue thoroughly dried by placing on the vacuum pump for 24 hours. 0.069 g of product is recovered.

α-Boc, Σ-Z-Lys-C(OH)-CH₂-C(O)—Leu-Arg(NO₂)-OMe (5)

To a solution of 0.500 g (1.03 mmol) and 4 and 0.470 g (1.26 mmol) of Leu-Arg(NO₂)—OMe.HCl in 30 ml of DMB is added 0.019 g (1.26 mmol) of HOBt in one portion. This addition is followed by the dropwise addition of 0.260 g (1.26 mmol) of DCC in 3 ml DMF. Finally, 0.003 ml of DIPEA is added and the solution stirred for 48 hours. The DMF is removed in vacuo and the residue dissolved in EtOAc. The solution is transferred to a separatory funnel and washed with 0.1N HCl, saturated NaHCO₃, and brine. The ethyl acetate layer is dried with MgSO₄, filtered and the solvent is removed. The residue is chromatographed on silica gel to afford 0.420 g of product. Rf=0.68-90/10 CH₂Cl₂/MeOH.

Σ-Z-Lys-C(OH)-CH₂-C(O)-Leu-Arg(NO₂)-OMe.HCl

To a solution of 5 (17.3 g, 0.022M) in 200 ml of dioxane is added 66.8 ml (0.220 m) of 3.3M HCl in dioxane. The mixture is stirred for 1 hour. At this time an additional 5 ml of 3.3M HCl in dioxane is added and the solution is stirred an additional 0.25 hour. The solvent is removed and the residue placed on the vacuum pump. The solid residue is triturated with ether under N₂ and filtered. 16.0 g of while solid is recovered.

Adoc-D-t-Bug-Phe-Lys(Z)-C(OH)-CH₂-C(O)-Leu-Arg(NO₂)-OMe (6)

To a solution of 16.0 g of the crude product from the previous reaction (0.022M) and 11.1 g of 1 (0.024M) in 300 ml of CH₂Cl₂ is added 6.69 ml (0.048M) of TEA dropwise followed by the dropwise addition of 3.64 ml (0.024M) of DECP. The solution is stirred overnight and the solvent is removed. The residue is dissolved in EtOAc and washed successively with 0.1N HCl, saturated NaHCO₃, and brine. The solution is dried and the solvent is removed to afford 26.6 g that is chromatographed on silica to afford 12.7 g of pure product. Rf=0.85, 90/10—CH₂Cl₂/MeOH.

Adoc-D-t-Bug-Phe-Lys(Z)-C(O)CF₂C(O)-Leu-Arg(NO₂)-OMe

To a slurry of 14.3 g (0.034M) of Dess-Martin periodinane in 1.15 L of CH₂Cl₂ is added 0.910 ml of dry pyridine, followed by the dropwise addition of 12.7 g (0.011M) of the product from the previous reaction in 2.3 L of CH₂Cl₂. The slurry is stirred for 2 hours and 58.7 g (0.24M) of Na₂S₂O₄ in saturated NaHCO₃ is added. The resulting solution is stirred for 0.5 hour. The phases are separated and the aqueous phase is extracted with ethyl acetate. The combined organic phases are dried and the solvent is removed to give 13.9 g of product that is used in the next reaction without purification (Rf=0.30—95/5 CH₂Cl₂/MeOH).

Adoc-D-t-Bug-Phe-Lys-C(O)CF₂C(O)-Leu-Arg-OMe.TFA (7)

To a solution of 13.4 g (0.012M) of the crude product from the previous reaction in 200 ml of dry DMF is added 6 g of palladium black. The resulting slurry is degassed for 0.5 hour. To this slurry is added 8 ml of 3.3M Hcl in dioxane. The reaction is placed on the Paar shaker and hydrogenated for 6 hours. The slurry is filtered through Celite and the solvent is removed. The residue is chromatographed on reverse phase HPLC (CH₃CN/H₂O/TFA) to afford 6.5 g product.

α-Boc, γ-Bn, γ-Z-Orn-C(OH)-CF₂-C(O)OEt (9)

To a solution of 5.67 g (0.087M) of activated zinc in dry THF is added 1.0 g of ethyl bromodifluoroacetate and the temperature is raised to reflux. At this time, 15.2 g (0.037 M) of —Bn, —Z— —Boc— Ornithinal 8 and 16.9 g (0.083M) of ethyl bromodifluoroacetate in THF is added, and the slurry allowed to reflux for 0.5 hour. The solution is cooled and quenched with saturated KHSO₄. The solution is diluted with EtOAc and washed with saturated KHS₄, saturated NaHCO₃ and brine. The solution is dried and the solvent removed. The residue is chromatographed on silica to give 6.58 g of product. Rf=0.22 99/1—CH₂Cl₂/ipa.

α-Boc, γ-Bn, γ-Z-Orn-C(OH)-CF₂-C(O)ONa

The ester 9 (0.965 g, 1.71 mmol) is dissolved in 15 ml MeOH and 1.71 ml of 1N NaOH is added. The solution is stirred for 3 hours and the solvent is removed. The residue is placed on the vacuum pump overnight and used in the next reaction as is (0.870).

αBoc, γ-Bn, γ-Z-Orn-C(OH)-CF₂-C(O)—Ala-Arg(NO₂)-OMe 10

To a solution of 0.870 g (1.56 mmol) of the crude product from the previous reaction and 0.579 g (1.90 mmol) of Ala-Arg(NO₂)—OMe.HCl in 80 ml of dry DMF is added 0.283 g (2.09 mmol) of HOBt, followed by the successive addition of 0.392 g (1.90 mmol) of DCC in 20 ml of DMF and 0.068 ml (0.39 mmol) of DIPEA. The mixture is stirred for 18 hours at room temperature and the solvent is removed. The residue is dissolved in EtOAc and washed with 0.1N HCl, saturated NaHCO₃ and brine. The solution is dried and the solvent is removed. Chromatography on silica gel yields 0.520 g of product (Rf=0.20 and 0.22).

α-Boc-Orn-C(OH)-CF₂-C(O)-Ala-Arg(NO₂)-OMe

The tripeptide 10 (0.338 g, 0.43 mmol) is dissolved in 10 ml of DMF and 0.15 g of palladium black is added. The slurry is degassed and 0.20 ml of 4.0M HCl in dioxane is added. The mixture is hydrogenated on the Paar apparatus overnight and filtered through Celite. The residue is redissolved in MeOH and 0.20 g of Pd(OH)₂ is added. The slurry is hydrogenated on the Paar for 24 hours at 50 psi. The slurry is filtered through Celite and the solvent is removed. The residue is used in the next reaction without purification.

α-Boc-Arg(Z)₂-C(OH)-CF₂-C(O)-Ala-Arg(NO₂)-OMe (11)

The crude amine (0.220 g, 0.39 mmol) is dissolved in THF and 0.325 g (0.91 mmol) of N,N-Bis-Z-S-methyl-isothiourea is added. To this solution is added 0.150 g Hg(OAc)₂ (0.47 mmol) and the mixture is stirred overnight. The solution is diluted with EtOAc and washed successively with 0.1 HCl, saturated NaHCO₃ and brine. The organic phase is dried and the solvent is removed. The residue is chromatographed on silica to afford 0.170 g of product as a mixture of diastereomers. Rf=0.60, 0.62—5% MeOH/CH₂Cl₂.

Adoc-D-t-Bug-Phe-Arg(Z)₂-C(OH)-CH₂-C(O)-Ala-Arg(NO₂)-OMe (12)

To a solution of 0.228 g (0.262 mmol) of 11 in 5 ml of dioxane is added 0.656 ml of HCl in dioxane. The solution is stirred for 1 hour and an additional 0.656 ml of HCl in dioxane is added. After stirring for an additional 1 hour, the solvent is removed and the residue is placed on the vacuum pump overnight. The hydrolysis product is dissolved in 5 ml of CH₂Cl₂ and combined with 0.120 g (0.262 mmol) of Adoc-D-t-Bug-Phe-OH. To this solution is added 0.073 ml (0.525 mmol) of TEA followed by the addition of 0.043 ml of DECP. The resulting mixture is stirred overnight. The solvent is removed and the residue chromatographed on silica to afford 0.086 g of product as a mixture of diastereomers. Rf=0.65, 0.68—4% ipa/CH₂Cl₂.

Adoc-D-t-Bug-Phe-Arg(Z)₂-C(O)-CF₂-C(O)-Ala-Arg(NO₂)-OMe

To a slurry of 0.094 g (0.16 mmol) of Dess Martin periodinane in 5 ml CH₂Cl₂ is added 0.091 g (0.052 mmol) of 12 dissolved in 0.5 ml via syringe. The mixture is stirred for 0.5 hour and 0.385 g (1.55 mmol) of Na₂S₂O₃ in saturated NaHCO₃ is added. After 0.5 hour, the solution is extracted with EtOAc and the organic phase is separated and dried with MgSO₄. Removal of the solvent yields 0.94 g crude product. Rf 0.68, 0.71— 4% ipa/CH₂Cl₂.

Adoc-D-t-Bug-Phe-Arg-C(O)-CF₂-C(O)-Ala-Arg-OMe.TFA (13)

The crude alcohol is dissolved in 2 ml DMF and 50 mg palladium black is added. The slurry is degassed and 0.040 ml of 4.0M HCl in dioxane is added. The mixture is hydrogenated on the Paar apparatus for 20 hours at 50 psi. The slurry is filtered through Celite and the solvent is removed. The residue is chromatographed on a reverse phase column (CH₃CN/H₂O/TFA) to afford 0.044 g of pure product.

N,N'-bis-carbobenzyloxy-S-methyl-isothiourea (14)

To a solution of S-methyl-isothiourea sulfate dimer (5.00 g, 18.0 mmol) in cold (0° C.) 1N NaOH (36.0 ml, 36.0 mmol) is added 11.3 ml (79.0 mmol) benzyl chloroformate and 79.0 ml (79.0 mmol) of 1N NaOH dropwise from separate addition funnels. The slurry is stirred for 0.5 hour at 0° C. and 1.5 hour at room temperature. The solution is extracted with ethyl acetate, dried with magnesium sulfate and the filtrate evaporated. Chromatography on silica gel yields 2.62 g pure product. Rf 0.40 (15% EtOAc/pet ether.

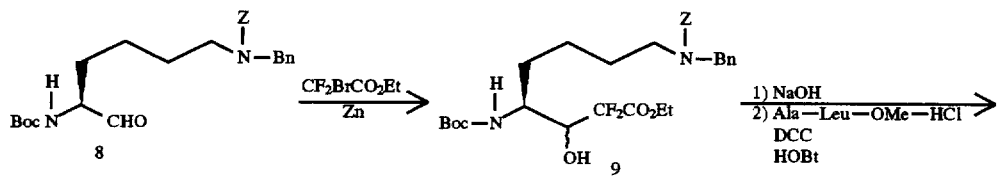

-continued

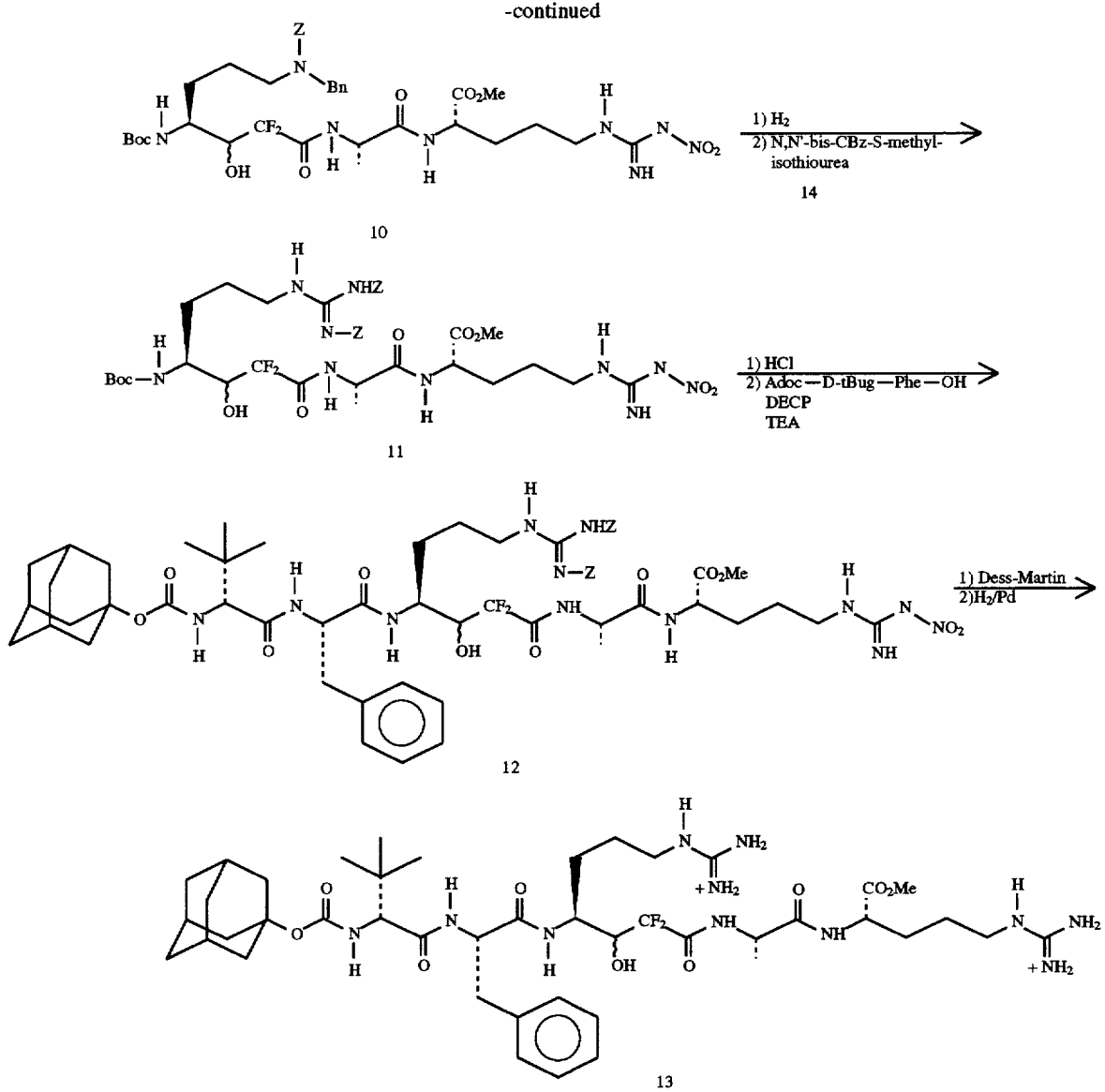

III. Synthesis of N-Terminating Linking Elements

Adac-D-t-Bug-Phe-OBn

To a solution of 5 ml of a 15% solution of phosgene in toluene under argon is added 0.140 ml TEA (1.00 mmol). This is followed by the addition of 0.112 g (0.750 mmol) of 1-adamantanamine in 1 ml toluene dropwise via syringe. The resulting slurry is stirred for 0.3 hour and the excess phosgene is removed by purging with argon. The solid is filtered off by suction through a sintered glass funnel and the solvent is removed. The residue is redissolved in dichloromethane and cooled to 0° C. under argon. To this solution is added 0.140 ml TEA (1.00 mmol) followed by 0.100 g (0.250 mmol) d-t-Bug-Phe-OBn.HCl in one portion. The resulting solution is removed. Chromatography on silica yields 0.350 g product.

Hydrogenation of this compound followed by subsequent coupling with hydrolysis product of 11 yields compounds that are successfully elaborated to an alternative N-terminating linking element.

Methods for Testing Activity of the Compounds

The following non-limiting procedures are methods for testing the anti-inflammatory and/or analgesic activity of the difluoro pentapeptide derivatives of the subject invention.

Several enzyme inhibition assays are known to be predictive of anti-inflammatory activity for compounds. Such enzyme assays are useful for measuring the activity of compounds of the subject invention. Such enzyme assays include the following: porcine pancreatic kallikrein (PPK) —see references A, E and F; human urinary kallikrein (HUK)—see references E and F; human plasma kallikrein (HPK)—see references B and E; human plasmin (HP)—see references B and C; and urokinase (UK)—see reference D. The indicated references, which are hereby incorporated herein by reference, are the following:

(A) Lottenberg, R., U. Christensen, C. M. Jackson & P. L. Coleman, "Assay of Coagulation Proteases Using Peptide Chromogenic and Fluorogenic Substrates," *Methods in Enzymology*, Vol. 80, Academic Press, New York, N.Y. (1981), pp. 341–361; (B) Geiger, R. "Kallikrein," *Methods* of *Enzymatic Analysis*, Vol. V. 3rd Edition, Bergmeyer, ed., Academic Press, New Nork, N.Y. (1984), pp. 129–143; (C) Morris, J. P., S. Blatt, J. R. Powell, D. K. Strickland & F. J. Castellino, "Role of Lysine Binding Regions in the Kinetic Properties of Human Plasmin," *Biochemistry*, Vol. 20, No. 17 (Aug. 18, 1981) p. 4811; (D) Wohl, R. C., L. Summaria & K. C. Robbins, "Kinetics of Activation of Human Plasminogen by Different Activator Species at pH 7.4 and 37° C." *The Journal Biological Chemistry*, Vol. 255, No. 5 (Mar. 10, 1980), pp. 2005–2013; (E) Okunishi, H., J. Burton & J. Spragg, "Specificity of Substrate Analogue Inhibitors of Human Urinary Kallikrein," *Hypertension*, Vol. 7, No. 3, Suppl. 1 (May-June, 1985), pp. I-72–75; (F) Amundsen, E., J. Putter, P. Friberger, M. Knos, M. Larsbraten & G. Claeson, "Methods for the Determination of Glandular Kallikrein by Means of a Chromogenic Tripeptide Substrate," In *Kinins-II part A*, Fuji, S., et al., eds., Plenum Press, New York, N.Y. (1979) pp. 83–95.

Another useful assay of activity is based on a method for determination of slow-binding enzyme inhibition disclosed in Imperiali, B. & R. H. Abeles, "Inhibition of Serine Proteases by Peptidyl Fluoromethyl Ketones," *Biochemistry*, Vol. 25 (1986) pp. 3760–3767. The method is modified as described below in order to study the slow binding inhibition of human plasmin, pig pancreatic kallikrein and human plasma kallikrein.

Reactions: The reaction mixtures contain 78 mM tris-HCl buffer, pH 7.4, 78 mM NaCl, 0.2 mg/ml bovine serum albumin, 0.2 mM S-2251 (D-Val-Leu-Arg-p-nitroanilide), 0.5 U/ml plasmin (1 μM), and variable concentrations of the test compound to be studied, in a total volume of 1 ml. The stock solution of plasmin is 1 U/ml in 50% glycerol. The absorbance change due to release of p-nitroaniline on enzymatic cleavage of S-2251 is monitored using an HP-8450 spectrophotometer system, set to measure $A^{400-410} - A^{470-490}$. The temperature is 30° C.

Calculations: $K_{obsd}$ and $v_s$ (steady state inhibited rate) are determined by fitting the progressive curve (first 20 min) to the integrated rate equation (i) using Labtech Notebook®, software. Estimated $k_i$ is calculated for each run from $v_s$ and the uninhibited rate v (equation ii), with (S)=0.2 mM and Km 0.77 mM.

(i) $A = v_s t - ((v_s - v_o)/k_{obsd})(1-\exp(-k_{obsd}t)) + A_o$ (ii) $k_1 = (I)/((v/v_s - 1)(1+(s)/km))$ A plot of kobsd vs test compound concentration for the different runs is then fit to a line, y=mx+b (see equation iii); $k_{on} = m(1+(S)/k_m)$ and $k_{off} = b$ are then calculated. Finally $k_1$ is calculated from equation iv.

(iii) $k_{obsd} = (I)/((v/v_s - 1)(1+(S)/km))$ (iv) $k_i = k_{off}/k_{on}$

Several in vivo assays are known to be predictive of the anti-inflammatory activity of compounds. Such in vivo assays are useful for measuring the activity of compounds of the subject invention. Such in vivo assays are disclosed in the following references which are hereby incorporated herein by reference:

Winter, C. A., E. A. Risley, G. V. Nuss, "Carrageenin-Induced Edema in Hind Paw of the Rat as an Assay for Antiinflammatory Drugs," *Proc. Soc. Exp. Biol., N.Y.*, Vol. 111 (1962), pp. 544–547; Vander Wende, C. & S. Margolin, "Analgesic Tests Based Upon Experimentally Induced Acute Abdominal Pain in Rats," *Federal Proceedings.*, Vol. 15 (1956), p. 494; Blackham, A., J. W. Burns, J. B. Farmer, H. Radziwonik, J. Westwick, "An X-Ray Analysis of Adjuvant Arthritis in the Rat. The Effect of Prednisolone and Indomethacin," *Agents and Actions*, Vol. 7/1 (1977), p. 145–151; Winter, C. A. & G. W. Nuss, "Treatment of Adjuvant Arthritis in Rats with Anti-Inflammatory Drugs" *Arthritis and Rheumatism*, Vol. 9, No. 3 (June, 1966), pp. 394–404; and Francis, M. D., K. Hovancik & R. W. Boyce, "NE-58095: A Diphosphonate Which Prevents Bone Erosion and Preserves Joint Architecture in Experimental Arthritis," *Int. J. Tiss. Reac.*, Vol. XI, No. 5 (1989), pp. 239–252.

Compositions and Methods of Using the Compounds

The following non-limiting examples exemplify contemplated compositions and uses for the subject invention.

EXAMPLE I

Tablets are made by conventional procedures, each having the following composition:

| Component | Quantity (mg) |
|---|---|
| Noc-D-t-Bug-Phe-Lys-C(O)CF$_2$C(O)-Leu-Arg-OMe | 400 |
| Microcrystalline cellulose | 200 |
| Pregelatinized starch | 200 |
| Povidone K-30 | 40 |
| Magnesium stearate | 20 |

One tablet is administered orally four times daily to a patient to alleviate inflammation in joints due to arthritis.

EXAMPLE II

A lotion is made by conventional procedures, the lotion having the following composition:

| Component | Quantity (%) |
|---|---|
| eBroc-D-tBug-Phe-Arg-C(O)CF$_2$C(O)-Gly-Arg-OMe | 2.5 |
| Glycerin | 4.0 |
| Methyl paraben | 0.2 |
| Propyl paraben | 0.1 |
| Carbopol 934 | 0.15 |
| NaOH | 0.46 |
| Cetyl stearyl palmitate | 1.0 |
| Stearic acid | 0.5 |
| Lanolin fatty acids | 0.5 |
| Cetyl alcohol | 3.0 |
| Zantham gum | 0.3 |
| Sodium stearoyl-2-lactolate | 0.75 |
| Isopropyl myristate | 2.0 |
| Water | q.s. |

One gram of the lotion is administered topically to the skin in the area of a burn twice daily to reduce inflammation and pain.

EXAMPLE III

A solution is made by conventional means, each 2 ml of solution having the following composition:

| Component | Quantity (mg) |
|---|---|
| Adoc-D-Phe-Phe-Lys-C(O)CF$_2$C(O)-D-Phe-Arg-OH | 80 |
| Benzalkonium chloride | 40 |
| Sterile aqueous saline solution | q.s. |

A 2 ml dose of the solution is injected intramuscularly to a patient with arthritis to reduce inflammation and pain.

EXAMPLE IV

A solution is made by conventional means, the solution having the following composition:

| Component | Quantity (%) |
|---|---|
| Adoc-D-t-Bug-Phe-Arg-C(O)CF$_2$C(O)-Ala-Arg-OH | 5.0 |
| Benzalkonium chloride | 0.02 |
| Sodium carboxymethyl cellulose | 0.01 |
| Aqueous saline solution | q.s. |

A 0.2 ml dose of the solution is administered by inhalation to a patient as needed to alleviate upper respiratory distress due to asthma.

While particular embodiments of the subject invention have been described, it will be obvious to those skilled in the art that various changes and modifications of the subject invention can be made without departing from the spirit and the scope of the invention. It is intended to cover, in the appended claims, all such modifications that are within the scope of this invention.

What is claimed is:

1. A compound, or pharmaceutically-acceptable salts or hydrates thereof, having the structure:

$$X-(CH_2)_n-V-Z-\underset{\underset{YO-C(O)-CH-NH-C(O)-CH-NH-C(O)-CF_2}{|}}{\overset{\overset{R^1}{|}}{CH}}-C(O)-NH-\underset{\underset{R^4}{|}}{\overset{\overset{R^2}{|}}{CH}}-C(O)-NH-\underset{\underset{C=O}{|}}{\overset{\overset{R^3}{|}}{CH}}$$

wherein:
(a) —X is selected from the group consisting of cyclic alkyl having from 4 to about 15 carbon atoms; branched alkyl having at least two branches having from 6 to about 15 carbon atoms; and aryl having from 6 to about 15 carbon atoms;

(b) n is an integer from 0 to 2;

(c) —V— is selected from the group consisting of —OC(O)—, —N(Q)C(O)—, —N(Q)C(S)—, —C(O)—, —SO$_2$— and —P(O)(OH)—;

(d) —Q is hydrogen; or straight or branched chain alkyl, saturated or unsaturated with 1 or 2 double bonds, having from 1 to 6 carbon atoms; or —Q and —X are covalently linked forming a cyclic moiety which includes the nitrogen to which —Q is bonded and from about 5 to about 20 carbon atoms;

(e) Z is —O— or —NH—; when V is —OC(O)—, —Z— is —NH—;

(f) —R$^1$ is selected from the group consisting of straight or branched alkyl, saturated or unsaturated with 1 or 2 double bonds, having from 1 to about 6 carbon atoms; cyclic alkyl, saturated or unsaturated with 1 or 2 double bonds, having from 3 to about 10 carbon atoms; and arylalkyl wherein the aliphatic portion is saturated and has 1 or 2 carbon atoms; and the carbon atom bonded to —R$^1$ is in either D or L configuration;

(g) —R$^2$ is selected from the group consisting of straight or branched alkyl, saturated or unsaturated with 1 or 2 double bonds, having from 1 to about 6 carbon atoms; cyclic alkyl, saturated or unsaturated with 1 or 2 double bonds, having from 3 to about 10 carbon atoms; and arylalkyl wherein the aliphatic portion is saturated and has 1 or 2 carbon atoms; and the carbon atom bonded to —R$^2$ is in either D or L configuration;

(h) —R$^3$ is —(CH$_2$)$_m$—A—NH$_2$ or —(CH$_2$)$_m$—A—B—C(NH$_2$)=NH wherein m is an integer from 1 to about 6, —A— is a covalent bond or p-phenyl or p-cyclohexyl, and —B— is a covalent bond or —NH—; and the carbon atom bonded to —R$^3$ is in L configuration;

(i) —R$^4$ is selected from the group consisting of straight or branched alkyl, saturated or unsaturated with 1 or 2 double bonds, having from 1 to about 6 carbon atoms; cyclic alkyl, saturated or unsaturated with 1 or 2 double bonds, having from 3 to about 10 carbon atoms; and arylalkyl wherein the aliphatic portion is saturated and has 1 or 2 carbon atoms; and the carbon atom bonded to —R$^4$ is in either D or L configuration;

(j) —R$^5$ is —(CH$_2$)$_m$—A—NH$_2$ or —(CH$_2$)$_m$—A—B—C(NH$_2$)=NH wherein m is an integer from 1 to about 6, —A— is a covalent bond or p-phenyl or p-cyclohexyl, and —B— is a covalent bond or —NH—; and the carbon atom bonded to —R$^5$ is in either D or L configuration; and (k) —Y is hydrogen or methyl.

2. The compound of claim 1 wherein —V— is —OC(O)— or —NHC(O)—, and —Z— is —NH—.

3. The compound of claim 2, wherein:
(a) n is 0 or 1;
(b) m is an integer from 1 to 5; and
(c) —R$^1$, —R$^2$ and —R$^4$ are selected from the group consisting of straight chain or branched alkyl having from 1 to about 5 carbon atoms, cyclic alkyl having from 3 to about 6 carbon atoms, and benzyl.

4. The compound of claim 3 wherein —X is saturated and unsubstituted bicyclo or tricyclo alkyl having from 8 to about 12 carbon atoms, or unsubstituted aryl having from about 8 to about 12 carbon atoms.

5. The compound of claim 4 wherein:
(a) —R$^3$ is —(CH$_2$)$_m$—A—NH$_2$, wherein —A— is a covalent bond, and m is from 3 to 5; and
(b) —R$^5$ is —(CH$_2$)$_m$—A—B—C(NH$_2$)=NH, wherein —A— is a covalent bond, —B— is —NH—, and m is from 2 to about 4.

6. The compound of claim 5 wherein —Y is methyl, —V— is —OC(O)—, and X is tricycloalkyl.

7. The compound of claim 6 wherein —R$^1$ and —R$^4$ are saturated and unsubstituted straight chain or branched alkyl, having from 1 to about 4 carbon atoms, and —R$^2$ is benzyl.

8. A compound, or the pharmaceutically-acceptable salts or hydrates thereof, having the structure:

$$X'-AA^1-AA^2-AA^3-CF_2-\overset{\overset{O}{\|}}{C}-AA^4-AA^5-OY$$

wherein:
(a) —AA$^1$— is selected from the group consisting of t-butylglycyl, valyl, isoleucyl, leucyl, cyclohexylglycyl, cyclohexylalanyl, phenylalanyl, naphthylalanyl, tryptophyl and adamantylglycyl;

(b) —AA$^2$— is selected from the group consisting of phenylalanyl, naphthylalanyl, cyclohexylalanyl, leucyl and isoleucyl;

(c) —AA$^3$— is selected from the group consisting of arginyl, homoarginyl, lysyl, p-guanidinophenylalanyl, p-amidinophenylalanyl and p-aminophenylalanyl;

(d) —AA$^4$— is selected from the group consisting of phenylalanyl, naphthylalanyl, cyclohexylalanyl, leucyl and isoleucyl;

(e) —AA$^5$ is selected from the group consisting of arginyl, homoarginyl, lysyl, p-guanidinophenylalanyl, p-amidinophenylalanyl and p-aminophenylalanyl;

(f) —X' is selected from the group consisting of adamantyloxycarbonyl, adamantoyl, fluorenylmethoxycarbonyl, adamantaneacetyl, adamantylaminocarbonyl, noradamantoyl, morpholinyl, homoadamantyloxycarbonyl, fenchyloxycarbonyl, isomenthyloxycarbonyl, isopinocamphanyloxycarbonyl, 3,5-dimethyladamantyloxycarbonyl, endo-bornyloxycarbonyl, naphthyloxycarbonyl and menthyloxycarbonyl; and (g) —Y is hydrogen or methyl.

9. The compound of claim 8 wherein —AA$^5$— is arginyl.

10. The compound of claim 9 wherein —AA$^3$— is lysyl.

11. The compound of claim 10 wherein —X' is adamantyloxycarbonyl.

12. The compound of claim 10 wherein:

(a) —AA$^1$— is selected from t-butylglycyl, valyl and isoleucyl;

(b) —AA$^2$— is phenylalanyl; and (c) —AA$^4$— is leucyl.

13. The compound of claim 12 wherein X' is selected from adamantyloxycarbonyl, endo-bornyloxycarbonyl and isopinocamphanyloxycarbonyl.

14. The compound of claim 13 wherein —AA$^1$— is t-butylglycyl, —X' is adamantyloxycarbonyl and —Y is methyl.

15. The compound of claim 10 wherein —Y is methyl.

16. A pharmaceutical composition comprising:

(1) a compound of any of claims 1, 5, 7, 8, 10, 14 or 15; and (2) a pharmaceutically-acceptable carrier.

17. A method of treating inflammation or pain comprising administering to a human or lower animal in need of such treatment a safe and effective amount of a compound of any of claims 1, 5, 8, 10 or 14.

* * * * *